United States Patent [19]

Brownlee et al.

[11] 4,026,305

[45] May 31, 1977

[54] LOW CURRENT TELEMETRY SYSTEM FOR CARDIAC PACERS

[75] Inventors: Robert R. Brownlee, State College; Frank O. Tyers, Hershey; Carl Volz, Sr., State College, all of Pa.

[73] Assignee: Research Corporation, New York, N.Y.

[22] Filed: June 26, 1975

[21] Appl. No.: 590,414

[52] U.S. Cl. .............. 128/419 PT; 128/2.1 A; 128/419 PG; 331/108 A; 331/113 R; 331/177 R; 340/248 D; 340/249

[51] Int. Cl.² .............................. A61N 1/36

[58] Field of Search ............... 128/2.05 R, 2.06 R, 128/2.1 AB, 419 E, 419 PG, 419 PT, 422, 419 PS; 340/248 R, 248 A, 248 D, 249, 253 R, 253 M, 253 Q; 331/108 A, 111, 113 R, 177 R, 177 V

[56] References Cited

UNITED STATES PATENTS

| 3,474,353 | 10/1969 | Keller, Jr. | 128/419 PG |
|---|---|---|---|
| 3,662,758 | 5/1972 | Glover | 128/419 E |
| 3,707,974 | 1/1973 | Raddi | 128/419 PG |
| 3,888,260 | 6/1975 | Fischell | 128/419 PS |

*Primary Examiner*—William E. Kamm
*Attorney, Agent, or Firm*—Cooper, Dunham, Clark, Griffin & Moran

[57] ABSTRACT

A system for telemetering the performance of an implanted cardiac pacer incorporating a low power, low voltage, frequency-voltage sensitive pulse generator which supplies a pulse-interval-modulated telemetry output and includes an astable complementary multivibrator in combination with a voltage clipping feedback network.

9 Claims, 4 Drawing Figures

4,026,305

LOW CURRENT TELEMETRY SYSTEM FOR CARDIAC PACERS

BACKGROUND

The present invention relates to a system for monitoring the operating condition of implanted electronic prosthetic devices such as cardiac pacemakers.

Periodic assessment of the operation of implanted electronic prosthetic devices such as cardiac pacers is desirable to ensure optimum performance and to guard against prolonged loss of proper functioning. Although many successful monitoring techniques have been in use, including the transmission of monitored data by telephone to fully equipped data centers, with the advent of longer implant lifetime through improved power sources, rechargeability, and the use of hermetic enclosures, the development of further monitoring methods is called for to adapt to the new devices. For example, modulation of the stimuli rate to monitor battery voltage in rechargeable cardiac pacers is technically undesirable because of the wider voltage variable encountered from the repeated recharging activity. Furthermore, it is generally desirable to employ voltage stable pacing oscillators so that pacing rate deviations can be utilized to determine impending component failure that would dictate emergency replacement. The data bandwidth employing pacemaker rate as the only data carrier also precludes the telemetry of other higher frequency pacemaker parameters. On the other hand, common RF telemetry techniques are not compatible with the growing use of hermetically sealed metallic enclosures. Additionally, means for non-disruptive or passive monitoring of ventricular controlled pacemakers is desirable. Presently adaptive pacemakers have to be forced to operate in a competitive fixed rate mode for monitoring, which is psychologically undesirable for some patients.

The present invention accordingly provides a pacemaker telemetry system incorporating an improved low power, low-voltage, frequency-voltage sensitive pulse generator for supplying pulse-interval-modulation telemetry of implant battery voltage. The oscillator is independent of the pacing function and allows for passive non-disruptive monitoring of the battery voltage and other pacemaker parameters. The system is also capable of monitoring dynamically separable functions, such as the pacing rate and refractory-delay-time of demand pacers and is compatible in frequency with electromagnetic transmission through metallic enclosures and with direct telecommunications.

SUMMARY

The present invention embodies a telemetry system including a telemetry pulse generator which is sensitive to input voltage and which comprises an astable complementary multivibrator in combination with a voltage clipping network. The nominal carrier center frequency of the pulse generator is pulse-interval-modulated by the voltage of the power cell and is selected to be on the low end of the telephone passband (250 cps) to provide in band transmission of the pulse harmonics and to minimize the attentuation encountered in transmission through an implanted metallic enclosure. The carrier may be further modulated via other voltage inputs at higher modulation rates for telemetry of refractory delay time and output pulse amplitude and/or width. The system operates passively in that normal pacemaker function need not be interrupted to perform measurements as is presently the case with ventricular controlled pacemakers.

DETAILED DESCRIPTION OF THE INVENTION

Figure 1:
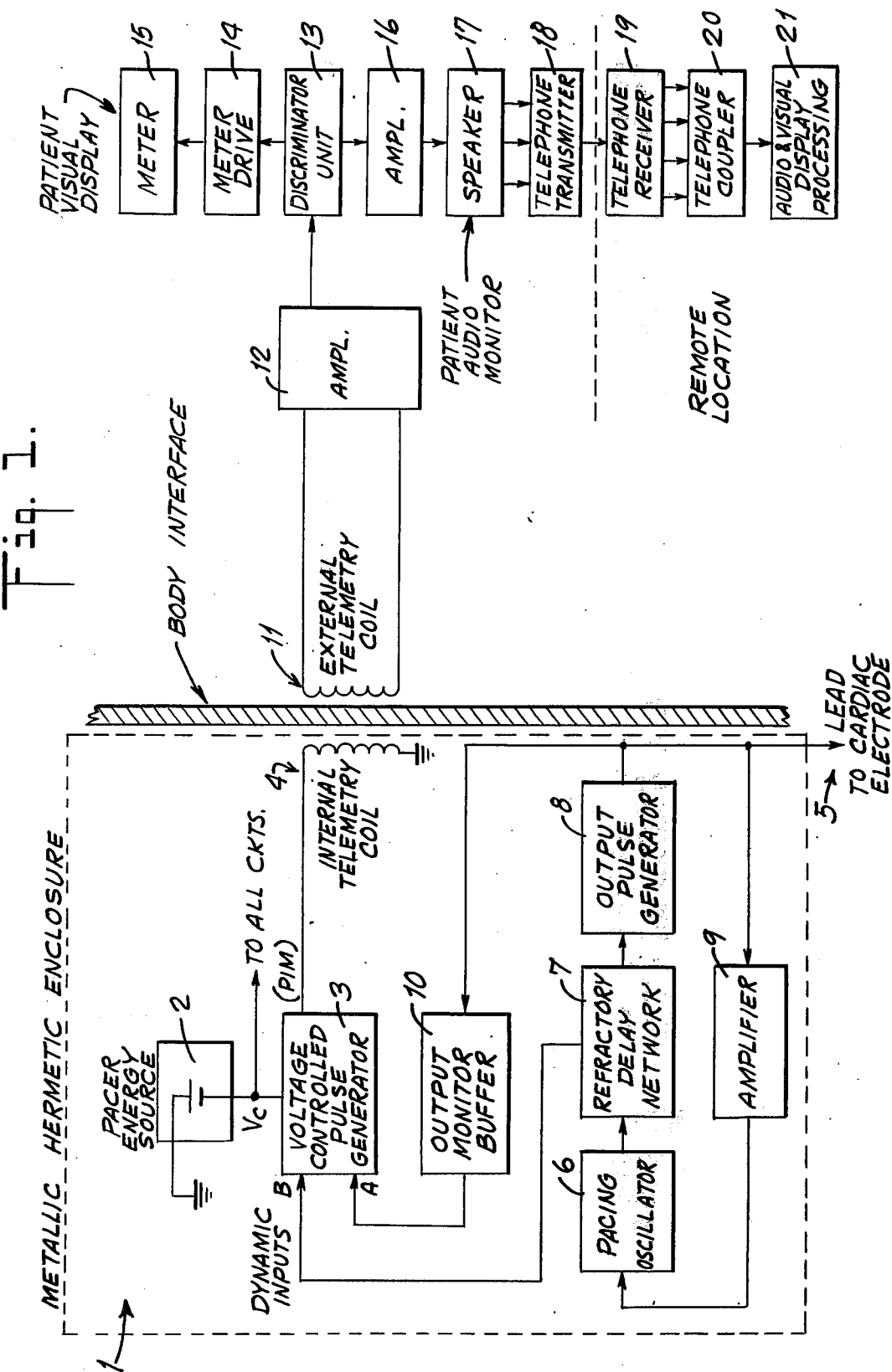
FIG. 1 is a block diagram of a telemetry system for a demand pacer in accordance with the present invention.

FIG. 1 illustrates a system in accordance with the present invention wherein the telemetry pulse generator is incorporated in an implanted adaptive pacemaker and a multiparameter monitoring arrangement is used. The implanted pacemaker 1, shown in dotted lines, comprises an hermetically sealed metallic enclosure containing a source of power in the form of a battery 2, the telemetry pulse generator 3, a telemetry output coil 4 and an electronic system for providing stimulating or pacing pulses to the cardiac electrode 5. The electronic system also provides the dynamic inputs A and B to the telemetry pulse generator 3, and more particularly comprises a pacing oscillator 6, a refractory delay network 7, and a pacing pulse generator 8, along with an amplifier 9 for feeding back the output pulses from generator 8 to the pacing oscillator 6.

The telemetry pulse generator 3 has a nominal carrier center frequency determined by the voltage $V_c$ of battery 2. The carrier frequency is further modulated via dynamic inputs A and B at higher modulation rates for telemetry of the refractory delay time and pacing pulse amplitude and/or width. It will be seen that the input at A is processed through a pacing pulse output monitor buffer 10 prior to injection into the generator 3 in order to provide an interface that prevents loading of the pacer output and to provide pulse expansion circuits that generate a modulation waveform compatible with the carrier frequency, as well as to provide recognition circuitry for sensing a lead break between the pacemaker and the cardiac electrode 5. Lead break monitoring is feasible by sensing significant changes in the pacing pulse amplitude or width accompanying the disconnection of the cardiac load from the pacemaker pacing pulse generator 8.

The input at B to the voltage-controlled telemetry pulse generator 3 is taken from the pacemaker refractory timing network 7. This input requires only resistive buffering since refractory delays are usually long relative to the pacing oscillator pulse interval (of the order of 100 milliseconds or greater as compared with 3.5 milliseconds) for oscillators of the present type.

The modulated output of the voltage-controlled telemetry pulse generator 3 is fed to telemetry coil 4 which may also be used as the charge-receive coil with a rechargeable power source. Coil 4 is electromagnetically coupled through the metallic enclosure wall and the body tissue of the host patient to an external telemetry receive coil 11. The external receive coil 11 which may also perform as a charging coil in a rechargeable system, receives the energy from the implanted coil 4 and provides it to an appropriate readout system. The readout system converts the energy picked up by coil 11 to an electrical signal that is amplified in amplifier 12 and fed to a discriminator unit 13. The signal in the discriminator unit 13 may then be processed through a meter driver 14 for local display on a meter 15 to the patient, or may be amplified in an amplifier 16 and fed to a local audio transducer such as speaker 17. The audio output of speaker 17 may be monitored by the patient or the speaker output may be fed to a telephone transmitter 18 for monitoring at a remote location. Telephone interfacing at the transmit and receive sites may be accomplished by either acoustic or electromagnetic coupling, and the signal from telephone receiver 19 may be passed through the telephone coupler 20 and undergo audio and visual display processing in the unit 21. The prime parameters which may easily be monitored by the patient locally are the pacemaker pulse rate and battery voltage. Using more complex receiving processing the refractory delay and output lead viability may be monitored locally or remotely. It is contemplated that the system also could incorporate patient pulse monitoring or EKG monitoring for verifying cardiac and pacemaker synchrony. Other well known "magnet" tests may be employed with the monitoring system to determine proper functioning of the fixed rate mode of demand pacers.

Figure 2:
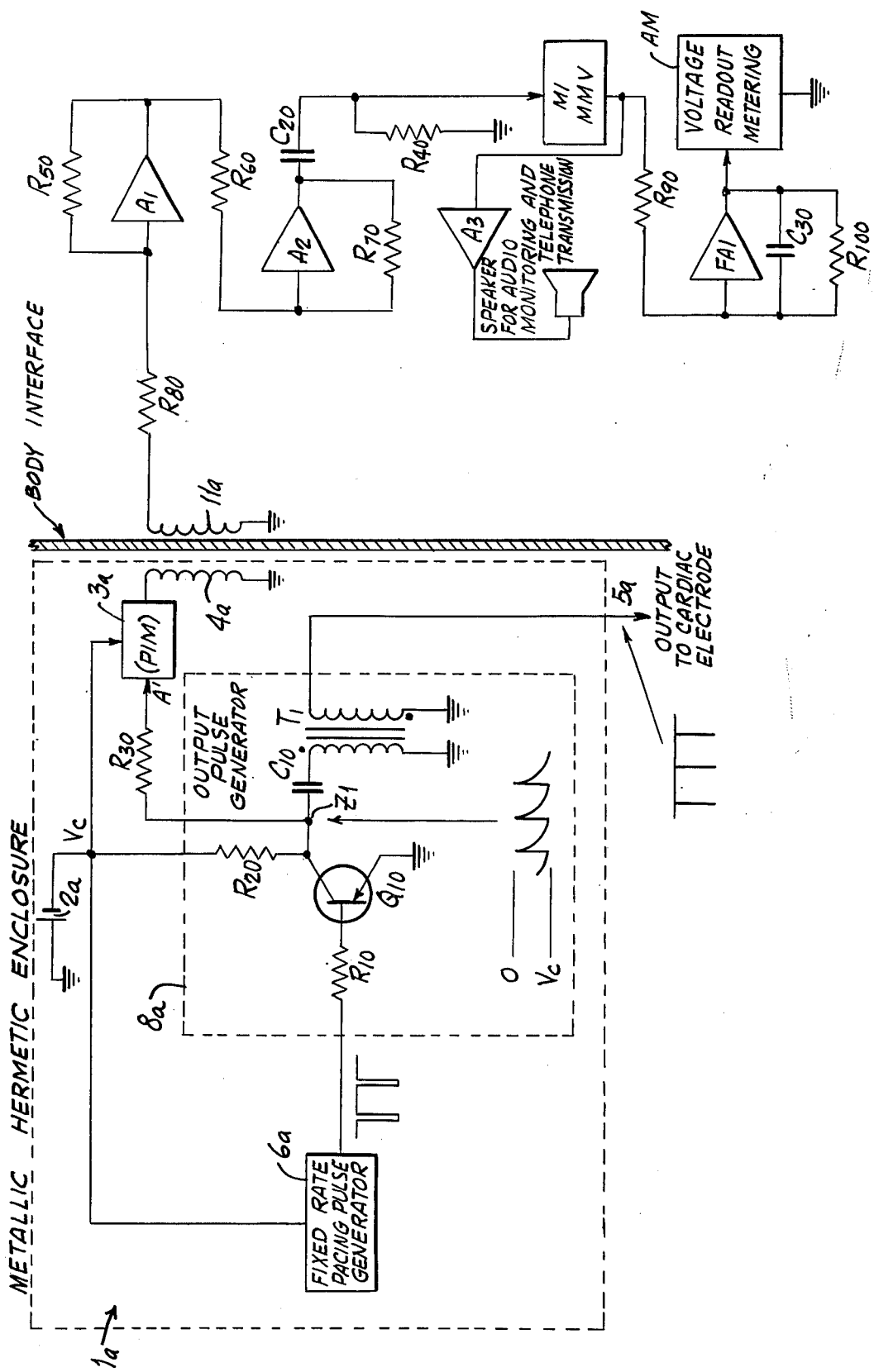
FIG. 2 is a schematic diagram of a telemetry system in accordance with the present invention used in connection with a fixed rate pacemaker.

FIG. 2 illustrates in greater detail a particular system in accordance with the present invention for monitoring battery voltage and pacing pulse rate in connection with a fixed rate pacemaker. This telemetry system is particularly suitable for use with a rechargeable, hermetically sealed fixed rate pacemaker having a metallic casing and in which fairly wide normal battery voltage variables preclude the use of pacemaker rate as the data carrier. Using small rate changes to discern large battery voltage variations would place stringent constraints on temperature and time drift specifications for the pacemaker circuitry if data ambiguities are to be avoided. Use of a large rate variable to telemeter the same data is physiologically undesirable. This telemetry generator is therefore preferably used with a separate stable pacing pulse generator such as disclosed in U.S. Pat. No. 3,971,389. This combination is fortunately feasible with rechargeability because the extra energy required for the monitoring function is replaceable although extra monitor energy drain should nevertheless be minimized. For use with non-rechargeable devices the telemetry generator may be switched on and off for monitoring by means of a magnet and reed switch combination or the like.

As shown in FIG. 2, the voltage $V_c$ of battery 2a is directly monitored by the pulse-interval-modulated (PIM) generator 3a and also acts as the energy source for the generator. The pacemaker pacing pulse rate is used to modulate the generator 3a by resistively coupling generator input A' through resistor $R_{30}$ to a node $Z_1$ in the pacemaker pacing pulse output generator 8a. Node $Z_1$ has a time-dependent voltage wave shape as illustrated in the figure compatible with the carrier frequency of generator 3a. It will be seen that the waveform at the monitoring point is synchronous with, but considerably wider than the final output wave form. Long exponential waveforms are available in most stimulator designs as inherent capacitor recharge functions in the timing circuitry.

More particularly, the output of the fixed-rate pacing pulse generator 6a is fed through resistor $R_{10}$ to the base of PNP transistor $Q_{10}$. The emitter of transistor $Q_{10}$ is grounded and its collector is coupled through resistor $R_{20}$ to the power source 2a, and through condenser $C_{10}$ to the output transformer $T_1$. Transformer $T_1$ provides pacing pulses to the cardiac electrode 5a.

The dynamic input from the collector of transistor $Q_{10}$ is converted by telemetry generator 3a into an output signal which is coupled electromagnetically from coil 4a through the wall of metallic enclosure 1a and the patient's tissue to the external telemetry coil 11a for further processing. For example, the received pulses may be amplified in amplifiers $A_1$ and $A_2$ and then differentiated in RC network $R_{40}C_{20}$ to form a trigger for multivibrator $M_1$. Multivibrator $M_1$ has a fixed pulse width but the pulse interval may be controlled by the trigger input interval and therefore by the output of the telemetry generator 3a. The average DC level of the pulse train is therefore interval dependent and represents a measure of the PIM frequency and accordingly the modulation data. Appropriate filtering and drive circuitry including amplifier $FA_1$ at the multivibrator output provide the discriminator function for detection of the data and its display on an microammeter AM. Conversion of the output of multivibrator $M_1$ to an audible signal for patient use in determining pacemaker rate and for audible telephone transmission of battery voltage and rate indications may be accomplished with common amplifier and speaker drive circuitry $A_3$. Resistors $R_{50}$, $R_{80}$ and $R_{60}$, $R_{70}$ determine the amplification factors of respective amplifiers $A_1$ and $A_2$ and resistors $R_{90}$, $R_{100}$ and condensor $C_{30}$ determine the amplification and filter characteristics of amplifier $FA_1$.

The metered display may be calibrated to read battery voltage directly, or could be labelled with colored safe and non-safe bands to indicate normalcy or the lack of it for patient use. Colored indicator lamps may be used in a similar manner. The metered display may also provide pacing rate data as a meter needle deflection that can be counted and clocked visually with the aid of a timepiece. With additional common digital techniques, rate may be independently displayed as a numerical readout and updated on a pulse-to-pulse basis.

At a remote location similar processing of telephone transmitted telemetry signals will yield the same data. Zero beat methods are presently in use in clinical tests wherein identical receiver hardware is used at both patient and data destination sites. A manually adjustable telemetry generator connected to a sending coil and coupled to a monitor console is employed by an operator at the data destination site for zero beating against the telephone signal. The zero beat is achieved by audio comparison of the acoustic signals by a trained operator and provides display of battery voltage at the remote site that is essentially identical to that observed by the patient on his console. The pacemaker rate is manually clocked by the operator from the audible modulated phone signal.

Figure 3:
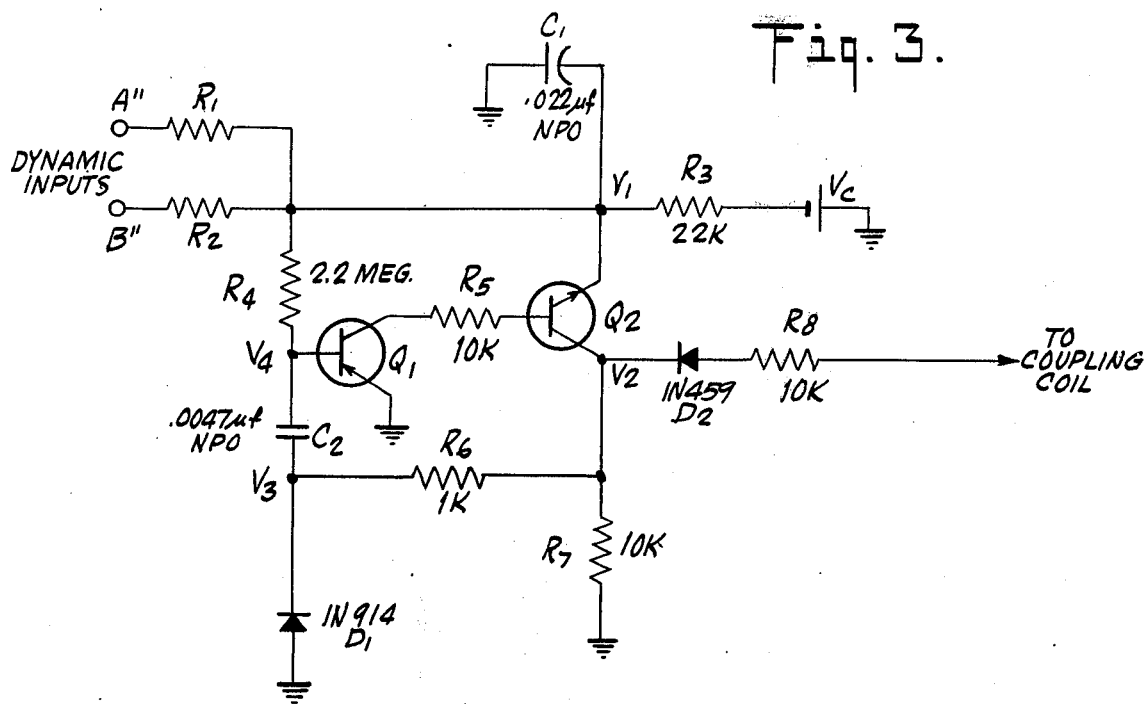
FIG. 3 is a circuit diagram of the low power, voltage controlled telemetry oscillator of the present invention.

A fundamental part of the present telemetry system for implant monitoring is the low-current, low-voltage pulse-interval-modulated generator 3 or 3a, which is shown schematically in FIG. 3. The circuit essentially comprises a complementary astable multivibrator with a clipped feedback network which provides a controlled and large frequency sensitivity to applied voltage changes. The important components for achieving the astable mode are the complementary paired transistors $Q_1$ and $Q_2$, RC networks $C_1R_3$ and $C_2R_4$, and resistors $R_5$ and $R_7$. Diode $D_1$ and resistor $R_6$ comprise the clipped feedback network which enhances the sensitivity of the pulse interval to voltage changes. Resistors $R_1$ and $R_2$ are data input buffers that allow controlled summation of dynamic modulation inputs in conjunction with the modulation from the supply voltage $V_c$. Dynamic inputs A″ and B″ should differ from each other in character and be distinguishable from supply variations to prevent data ambiguities.

This telemetry pulse generator produces short pulses separated by a relatively long interval. During a pulse, both transistors $Q_1$ and $Q_2$ are turned "on." For the interval between pulses both transistors are "off" and do not draw current, although some energy is consumed in the recharging of capacitors $C_1$ and $C_2$ through the respective resistive networks. To minimize the energy drain, the ratio of on to off time is made small, of the order of about 0.1, with a resulting operating current of about 5 microamps at 1.4 volts.

By way of understanding the oscillatory sequence of the generator more fully, consider that just prior to the on condition, the voltage at $V_1$ on capacitor $C_1$ has attained a value near the source voltage $V_c$ and capacitor $C_2$ has charged through resistor $R_4$ to a value at $V_4$ approaching the one requirements of transistor $Q_1$ and therefore transistor $Q_2$ through resistor $R_5$. When the voltage at $V_4$ reaches an on value the voltage at $V_2$ jumps to a value near that at $V_1$ through saturation conduction of transistor $Q_2$. Saturation conduction is ensured by the added base drive supplied by the positive feedback via resistor $R_6$ and capacitor $C_2$ as the voltage at $V_2$ increases toward that at $V_1$. During the on period, condenser $C_2$ discharges and supplies base drive to transistor $Q_1$. Simultaneously with the discharge of condenser $C_2$, condenser $C_1$ is also discharging to a value dependent on the circuit loading at resistor $R_3$.

When the base drive of transistor $Q_1$ is depleted by decay of the charge on condenser $C_2$ and the insufficiency of base drive current via resistor $R_4$ because of the voltage decay at $V_1$, the resultant loss of saturation of transistor $Q_2$ creates the condition to ensure a reversal to the off state. A drop in voltage at $V_2$ to a value below the diode voltage at $V_3$, because of the loss of saturation through transistor $Q_2$ and the lowered voltage level at $V_1$ results in a rapid transition to the off state by way of the positive feedback through resistor $R_6$ and condenser $C_2$. In the off state condenser $C_1$ begins to charge toward supply voltage $V_c$ and condenser $C_2$ begins to charge toward the voltage at $V_1$ through resistor $R_4$. When the voltage at $V_4$ again reaches a value sufficient to turn on transistors $Q_1$ and $Q_2$ the cycle is repeated.

It will be seen that without the feedback network provided by resistor $R_6$ and diode $D_1$ and with condenser $C_2$ returned directly to the collector of transistor $Q_2$ the multivibrator is relatively supply independent. The supply independence occurs as a result of the fact that as the supply voltage is changed the effective positive feedback value via condenser $C_2$ is also changed as a counterbalance. More particularly, it will be seen that as the driving voltage for charging condenser $C_2$ is changed, the excursion of the voltage at the base of transistor $Q_1$ required for reaching a state change to an on condition is simultaneously modified in a compensatory way because of the changes in the excursion of voltage at $V_2$ with the supply voltage changes. The voltage clipping network comprising resistor $R_6$ and diode $D_1$ limits the compensating symmetry by not allowing the changes in the total excursion of voltage at $V_2$ to be reflected as an initial condition (post pulse) on condenser $C_2$. Drive changes with supply voltage changes for charging condenser $C_2$ via resistor $R_4$ are therefore effective in changing the pulse interval and a high sensitivity of the frequency dependence of voltage is achieved.

The circuit temperature sensitivity has been found to reflect a less than +1% per °F readout error which is quite adequate for the contemplated implant environment and the general requirements for battery monitoring.

Diode $D_2$ and resistor $R_8$ provide buffering to the monitor coupling coil (4,4a). Resistor $R_8$ serves to limit the loading of the coupling coil on the generator and diode $D_2$ prevents transmission of ambiguous data at very low supply voltage levels, for example 0.75 volts and below.

Figure 4:
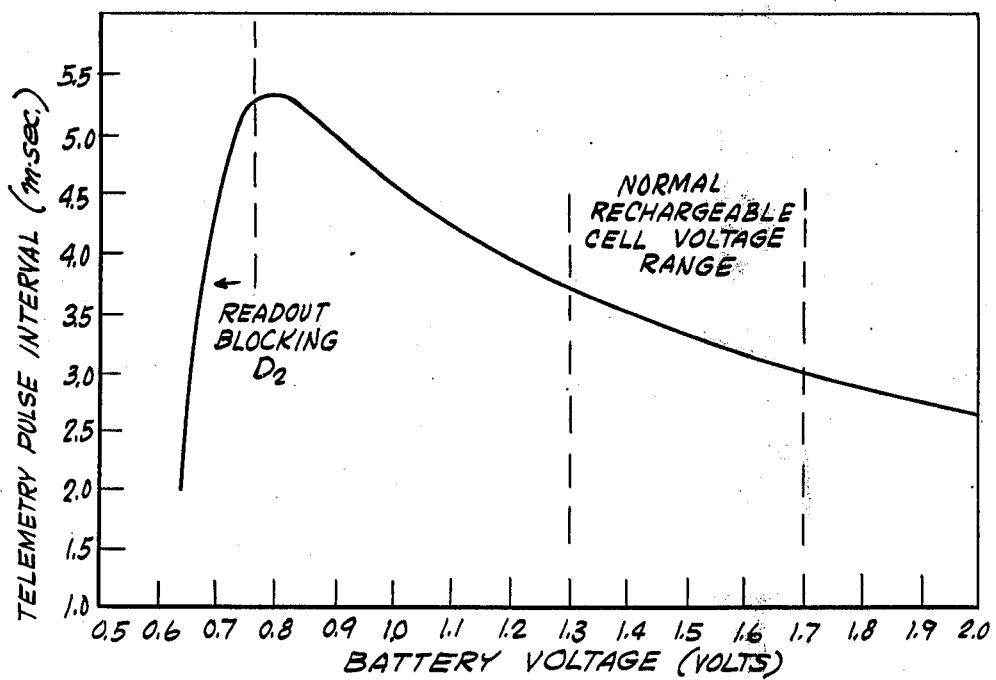
FIG. 4 is a plot of the output pulse interval in milliseconds of the generator of FIG. 3 as a function of battery voltage.

FIG. 4 is a plot of the output pulse interval against supply voltage variation for the circuit shown in FIG. 3. Suitable circuit component values, as shown in FIG. 3, are as follows: $C_1$ = 0.022 microfarad; $C_2$ = 0.0047 microfarad; $R_3$ = 22 K ohms; $R_4$ = 2.2 megohms; $R_6$ = 1 K ohm; and $R_5$, $R_7$ and $R_8$ = 10 K ohms. Diode $D_1$ is a 1N914 type and diode $D_2$ is a 1N459 type.

FIG. 4 shows the function reversal and potentially ambiguous data below a supply voltage of 0.75 volts. The dotted line on the curve at that voltage shows the blockage point of diode $D_2$ that limits transmission of erroneous data. The function shown in FIG. 4 is not ideally linear over its monotonic range. Expected normal cell voltages fall in a smaller range as indicated. A best linear fit over the short usage span is quite satisfactory, that is less than 2% error, and voltages outside that range represent the regions which require action such as a recharging maintenance activity.

It will thus be seen that an improved telemetry system for use in rechargeable and nonrechargeable pacemakers of the adaptive or fixed-rate type is provided which is operated at low-voltage and low-power drain, and which has a controlled and large frequency sensitivity to applied voltage changes. It will also be appreciated that the polarity of the power source may be reversed with respect to the connections shown in FIG. 3, the transistors appropriately changed and the diodes turned around without essentially altering the operation of the circuit.

It is further contemplated that the present telemetry system may find wide application for indirect or non-invasive monitoring of sealed systems containing batteries such as in the fields of oceanography, industrial testing and the like.

We claim:

1. Apparatus for telemetering the condition of a component in a cardiac pacer implanted in a patient, which pacer provides stimulating pulses to the heart of the patient, comprising:
   voltage means in said pacer for producing a voltage output signal indicative of the condition of a component of said pacer;
   a ground;
   pulse producing means in said pacer for receiving said voltage output signal and producing an output train of electrical pulses independent of said stimulating pulses, said pulse producing means comprising a complementary astable multivibrator comprising:

a first transistor; and a second transistor of opposite conductivity type from said first transistor and having its emitter directly connected to said ground;

means in said pacer for modulating said output train of electrical pulses in accordance with the magnitude of said voltage output signal, said modulating means comprising:

a resistor inserted between the collector of said first transistor and the base of said second transistor; and a diode inserted between the base of said second transistor and said ground with its anode directly connected to said ground;

means in said pacer for electrically transmitting said modulated output train of electrical pulses out of said pacer and said patient; and means external to said patient for receiving said electrically transmitted output train of electrical pulses.

2. Apparatus as in claim 1 wherein said electrically transmitting means comprises a second diode, a resistor and a transmitting coil respectively connected in series with each other, and with the cathode of said second diode being directly connected to the collector of said first transistor and with said transmitting coil directly connected to said ground.

3. Apparatus as in claim 1 wherein said voltage means is connected to the emitter of said first transistor for supplying said voltage output signal thereto, and further comprising another voltage means for supplying another voltage output signal to the emitter of said first transistor.

4. Apparatus as in claim 1 wherein said voltage means is a power cell of the pacer.

5. Apparatus for providing a continuous train of electrical output pulses whose timing is sensitive to variations in input voltages comprising:

a ground;

a first transistor;

a second transistor of opposite conductivity type from said first transistor and having its emitter grounded;

first means for connecting the base of said first transistor to the collector of said second transistor;

second means for connecting the emitter of said first transistor to the base of said second transistor;

third means for connecting the emitter of said first transistor to a source of input voltage;

fourth means for connecting the emitter of said first transistor to ground;

fifth means for connecting the collector of said first transistor to ground;

sixth means for connecting the base of said second transistor to said fifth means;

seventh means connected to the collector of said first transistor for conducting said electrical output pulses; and wherein said first, second, third, fifth, sixth and seventh means each comprise a resistor, said fourth means comprises a condenser and said sixth means further comprises a condenser, and said fifth and seventh means each further comprise a diode, the former of which has its anode grounded and the latter of which has its cathode connected directly to the collector of said first transistor.

6. Apparatus as in claim 5 further comprising eighth means for connecting the emitter of said first transistor to a second source of input voltage.

7. A telemetry pulse generator system for use in cardiac pacers, which generator system is pulse interval modulated by variations in input voltage comprising:

power cell means having a first pole and a second pole with a voltage difference between them for supplying an input voltage;

a first transistor;

a first resistor inserted between the emitter of said first transistor and the first pole of said power cell for connecting said first transistor to said input voltage;

a first condenser inserted between the emitter of said first transistor and the second pole of said power cell;

a second transistor of a conductivity type opposite to that of said first transistor and having its emitter connected directly to said second pole;

a second resistor inserted between the base of said first transistor and the collector of said second transistor;

a third resistor inserted between the base of said second transistor and the emitter of said first transistor;

a fourth resistor inserted between the collector of said first transistor and said second pole;

a fifth resistor and a diode connected in series between the collector of said first transistor and said second pole with the anode of said diode connected directly to said second pole;

a second condenser inserted between the base of said second transistor and the junction between said fifth resistor and said diode; and means connected to the collector of said first transistor for conducting interval modulated output pulses.

8. A system as in claim 7 wherein said means for conducting output pulses comprises a sixth resistor and a second diode with its cathode connected directly to the collector of said first transistor.

9. A system as in claim 7 further comprising means connected directly to the emitter of said first transistor for conducting a second modulating input voltage thereto.

* * * * *